United States Patent [19]

Juhasz

[11] Patent Number: 4,817,594
[45] Date of Patent: Apr. 4, 1989

[54] WOUND DRESSINGS WITH ELECTRICALLY CONDUCTIVE LAYERS

[76] Inventor: Laszlo Juhasz, 18 Clovelly Avenue, London, Great Britain, NW9 6DT

[21] Appl. No.: 2,665
[22] PCT Filed: Apr. 18, 1986
[86] PCT No.: PCT/GB86/00218
   § 371 Date: Dec. 9, 1986
   § 102(e) Date: Dec. 9, 1986
[87] PCT Pub. No.: WO86/05971
   PCT Pub. Date: Oct. 23, 1986

[30] Foreign Application Priority Data

Apr. 18, 1985 [DE] Fed. Rep. of Germany ....... 8509978

[51] Int. Cl.⁴ .................... A61F 13/00; A61F 15/00
[52] U.S. Cl. .................................. 128/155; 128/156; 128/783; 128/464; 604/20; 604/304; 204/415
[58] Field of Search ............... 128/155, 156, 82.1, 128/783, 784, 785; 604/358, 360, 378, 304, 375, 20; 428/464; 204/415

[56] References Cited

U.S. PATENT DOCUMENTS

| | | | |
|---|---|---|---|
| 2,690,415 | 9/1954 | Shuler | 167/84 |
| 3,299,890 | 1/1967 | Parker | 128/156 |
| 3,340,875 | 9/1967 | Dudley et al. | |
| 3,515,126 | 6/1970 | Fregert | 604/307 |
| 3,930,882 | 9/1975 | Augurt | 128/155 |
| 3,939,838 | 2/1976 | Fujinami et al. | |
| 4,088,132 | 5/1978 | Wood et al. | |
| 4,203,435 | 5/1980 | Krull et al. | 128/156 |
| 4,314,554 | 2/1982 | Greatbatch | 604/20 |
| 4,547,195 | 10/1985 | Jackson | 604/359 |
| 4,595,001 | 6/1986 | Potter | 128/156 |
| 4,596,738 | 6/1986 | Metcalfe | 128/156 |
| 4,619,252 | 10/1986 | Ibbott | 128/82.1 |
| 4,699,146 | 10/1987 | Sieverding | 128/156 |
| 4,715,857 | 12/1987 | Juhasz et al. | 128/156 |
| 4,722,354 | 2/1988 | Axelgaard et al. | 128/783 |

FOREIGN PATENT DOCUMENTS

| | | |
|---|---|---|
| 0053936 | 6/1982 | European Pat. Off. |
| 0099758 | 2/1984 | European Pat. Off. |
| 2380688 | 9/1978 | France. |
| 386067 | 1/1933 | United Kingdom. |
| 1301101 | 12/1972 | United Kingdom. |
| 2092006 | 8/1982 | United Kingdom. |
| 2127389 | 4/1984 | United Kingdom. |

Primary Examiner—Richard J. Apley
Assistant Examiner—Paul Prebilic
Attorney, Agent, or Firm—Jeffers, Hoffman & Niewyk

[57] ABSTRACT

An integral anti-bacterial wound dressing, which comprises, five layers which are, in order (except that layers 2 and 3 and 4 may be in either order),
(1) a first layer of a permeable material;
(2) a layer of a semi-permeable material;
(3) a layer of an electrically-conductive material, in the form of an open mesh;
(4) a layer of charcoal fabric; and
(5) a non-adherent wound-facing second layer of a permeable material;

in which layers 1, 2 and 5 substantially co-extensive and surround the charcoal fabric (3), and are bound together in the surrounding area.

27 Claims, 1 Drawing Sheet

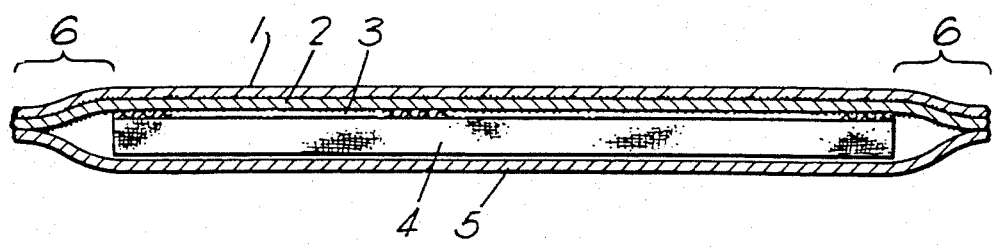

WOUND DRESSINGS WITH ELECTRICALLY CONDUCTIVE LAYERS

The present invention relates to anti-bacterial wound dressings. In particular, it relates to integral dressings which can be used to cover contaminated, discharging malodorous wounds, and assist in their treatment. More specifically, it relates to wound dressings comprising activated carbon.

The utility of carbonised fabric in surgical dressings has been appreciated for over 50 years. GB-A-0386867 discloses surgical dressings comprising woven or entangled carbonised fibres. Such dressings are also disclosed as supports for therapeutic or antiseptic materials and it is stated that "the dressings will hold in considerable quantities iodine, formol, lime, oxygen, bacillary toxins, and the like". The use of, say, iodine, in such dressings appears to be a consequence of the adsorptive characteristics of charcoal cloths. GB-A-1301101 discloses a particularly useful, and commercially used, process for preparing activated carbon products in fibrous form. Rayon, for example, is impregnated with a solution of inorganic halides and then activated in a controlled heating step. The products, i.e. activated carbon cloth or felts, adsorb both organic materials and bacteria.

Surgical dressings using activated charcoal impregnated with anti-bacterial agent, within an envelope of permeable material, are disclosed in EP-A-0053936; the adsorptive sites of the activated charcoal are no more than 20% saturated with an anti-microbial agent, preferably iodine.

A disadvantage of such a dressing is that the agent incorporated in the dressing inherently limits the bacteria-adsorbing characteristics of the charcoal and could adversely affect wound healing. Further, the charcoal cloth can easily fragment, and carbon particles can find their way into the wound.

EP-A-0099758 discloses a three-layered composite (but not integral) wound dressing comprising a semi-permeable membrane, a permeable supporting and reinforcing layer, and a non-stick, self-sealing biodegradable tissue interface. The permeable layer may be an activated carbon cloth.

GB-A-2127389 discloses a surgical dressing comprising activated charcoal cloth or felt which has been produced so that it contains elemental silver distributed throughout. Such a product is at least bacteriostatic, but may not "fix" bacteria or facilitate wound healing.

It is an object of the invention to provide an anti-bacterial wound dressing which has an integrated structure and assists wound healing. In other words, the wound dressing should provide a barrier against bacterial contamination and mechanical injury, and also provide controlled water vapour transmission and controlled heat loss. It is a further object of the invention to provide a wound dressing which is not merely therapeutic but also bactericidal.

An integral anti-bacterial wound dressing according to the present invention comprises five layers which are, in order (except that layers 3 and 4 may be in either order),
(1) a first layer of a permeable material;
(2) a layer of a semi-permeable material;
(3) a layer of an electrically-conductive material, in the form of an open mesh;
(4) a layer of charcoal fabric; and
(5) a non-adherent wound-facing second layer of a permeable material;
in which layers 1, 2 and 5 are substantially co-extensive and surround the charcoal fabric (3), and are bound together in the surrounding area.

The accompanying drawing is an enlarged cross-sectional side view (not to scale) of a wound dressing which is an illustrative embodiment of the present invention.

The drawing shows a first layer of permeable material 1, a layer of a semi-permeable material 2, an open mesh 3 which is electrically-conductive, an activated charcoal fabric 4 and a second layer of permeable material 5. The permeable layers 1 and 5 and the semi-permeable layer are bonded at the border area 6 of the product, i.e. around the fabric 4.

It is intended that layer 5 should come into contact with a wound. In this position, bacteria in the atmosphere which come into contact with layers 1 and 2 are prevented from passing to the wound.

The integral nature of the dressing according to the present invention may be provided by heat-sealing or otherwise bonding layers 1, 2 and 5 in the area surrounding layer 4. Depending on the extent of this area, the charcoal fabric is more or less loosely held.

Alternatively, and as is often preferred, a semi-permeable material having double-sided adhesive properties is used. In consequence, via the semi-permeable material (through the open mesh if it is between layers 2 and 4), one entire surface of the charcoal fabric is bonded to the first layer of permeable material. The two layers of permeable material are bonded together in the area which borders the charcoal fabric (through the open mesh if it is present in the border area). The only area of non-adherence between pairs of adjacent layers in the dressing (shown clearly in the drawing) is over the adjacent faces of the charcoal fabric and layer 5; the opposite face of layer 5 is entirely suitable as that intended to contact the wound, in use. If desired, the double-sided adhesive properties are apparent only at elevated temperature, e.g. because the semi-permeable material is thermoplastic and can be made tacky, say, at 40 to 60 C., and may be induced by applying a heat-press.

A wound dressing of the invention may carry a marker indicating the opposite side to the wound-facing surface.

The "enveloping" layers of permeable material may be of different or, often, the same material. Examples of suitable materials are natural or synthetic rubber, nylon, polyester, polyurethane and rayon acetate, and other suitable synthetic polymers. The material should be in the form of a fabric or film having a pore size of, say, 50 to 500 $\mu$m, e.g. about 150 to 200 $\mu$m. The wound-facing layer may instead be biodegradable, e.g. of a collagen or a collagen-alginate material.

The open mesh may be of a material such as nylon which has been treated by impregnation with a metal such as silver. The mesh size will usually be sufficient to allow the semi-permeable material to come into contact with the charcoal fabric. The mesh size is, for example, 200 to 1000, and often 250–300, $\mu$m.

The mesh is electrically-conductive. A wound dressing of the invention may be provided with means for applying a voltage, or at least an aperture through the first layer of permeable material and the semi-permeable material, so that the mesh is partially exposed, allowing the attachment of such means. The application of a voltage to the dressing, in use, provides one or more desirable effects. A negative direct current enhances tissue growth. Alternating current can also enhance the would-healing process, providing transcutaneous stimulation and giving post-operative pain relief. Further, if the mesh is silver-impregnated and a positive direct current is applied, silver ions are driven into the wound and inhibit bacterial growth. In this case, the mesh is effectively bactericidal.

In order to ensure good conductivity, a dressing of the invention may be hydrated prior to use, e.g. with isotonic saline. The hydrated dressing, suitably packaged, may be marketed as such.

Within the scope of the invention, the mesh and the charcoal fabric may be in either order, i.e. the layers are in the order 1-2-3-4-5 or 1-2-4-3-5. The former is preferred.

The charcoal fabric is, for example, a cloth or fabric of the activated type, e.g. prepared as described in GB-A-1301101. It is preferably a woven, knitted or non-woven fabric of activated carbon, but any activated charcoal fabric, made from, e.g. paper or other cellulosic material, may be used. For ease of handling, the charcoal cloth may be laminated to a substrate of any suitable material, e.g. a polyester viscose such as FBR 33 (available from BFF), but this is not critical.

The semi-permeable material may be thermoplastic, e.g. having a softening point of 70 to 120 C.; suitable materials are polyamides such as polycaprolactam and other "nylons", and also polycarbonates. Further, inherently adhesive semi-permeable materials are known, e.g. in the form of a "transfer tape". A double-sided transfer tape, having a pore size of less than 50 $\mu$m, derived from rayon acetate and polyurethane, is available from DRG or the 3M Company Ltd. Alternatively, semi-permeable adhesive material can be sprayed on to double release papers or, using a single release paper, on to the outer dressing layer.

Preferably, the semi-permeable material has a pore size of less than 20 $\mu$m. It should provide water vapour transmission of 200 to 2000 g/m$^2$/24 h, for the dressing at the standard relative humidity of 100% and standard temperature of 37° C., as a whole. The effective pore size of the dressing may be less than 2 $\mu$m.

The size of a wound dressing of the invention may be defined as desired. For example, the charcoal fabric may be about 140×90 mm and the other three layers each about 150×100 mm in area, so that the border around the charcoal fabric is about 10 mm wide. An alternative embodiment comprises a relatively wide border on two sides of the charcoal fabric, so that the product has more the appearance of a strip. Again, the dressing can be formulated as a bandage. For use, the dressing may be provided together with a release liner.

A product of the invention has anti-bacterial characteristics in that it adsorbs bacteria, reduces bacterial growth (by limiting oxygen availability), and provides a bacterial barrier, thereby minimising external and cross-contamination. The dressing has wound-healing characteristics because it controls water vapour transmission, thereby maintaining a humid environment which allows the natural wound-healing processes to function.

The wound-facing permeable layer is essentially non-adherent to the wound. The dressing can be adsorbent with respect to exudate, and eliminate offensive odours.

A primary advantage of a wound dressing of the invention is that it is anti-bacterial and assists wound management. It can be used for the treatment of infected and discharging, ulcerated and permanent, cancerous and malodorous, and contaminated and burn wounds. Its structure is integrated. In particular, the charcoal fabric is bound over its area; fraying, which occurs if such a material is merely loosely held, and which potentially leads to carbon fabric particles being shed into a wound, is prevented.

I claim:

1. An integral anti-bacterial wound dressing which comprises, five layers which are, in order except that layers (3) and (4) may be in either order,
   (1) a first layer of a permeable material;
   (2) a layer of semi-permeable material;
   (3) a layer of an electrically-conductive material, in the form of an open mesh;
   (4) a layer of charcoal fabric; and
   (5) a non-adherent wound-facing second layer of a permeable material;
   in which layers (1), (2) and (5) are substantially co-extensive and surround the charcoal fabric (4), and are bound together in the surrounding area.

2. A wound dressing according to claim 1, wherein the charcoal fabric (4) is an activated carbon fabric.

3. A wound dressing according to claim 1, wherein the semi-permeable material has a pore size of less than 20 $\mu$m.

4. A wound dressing according to claim 1, wherein the order of the five layers is (1)-(2)-(3)-(4)-(5) and the semi-permeable material is adhesive, whereby layer (1) is bound through the open mesh to the charcoal fabric and, in the area surrounding the charcoal fabric (4), to layer (5).

5. A wound dressing according to claim 1, characterized by water vapour transmission of 200 to 2000 g/m$^2$/24 h at 100% relative humidity and 37° C.

6. A wound dressing according to claim 1, wherein the electrically-conductive mesh comprises a silver-impregnated material.

7. A wound dressing according to claim 1, provided with means for applying a voltage.

8. A wound dressing according to claim 1, wherein the order of the five layers is (1)-(2)-(3)-(4)-(5).

9. A wound dressing according to claim 2 wherein the semi-permeable material is adhesive and the order of the five layers is (1)-(2)-(3)-(4)-(5), whereby layer (1) is bound through the open mesh to the charcoal fabric and, in the area surrounding the charcoal fabric (4), to layer (5).

10. A wound dressing according to claim 3 wherein the semi-permeable material is adhesive and the order of the five layers is (1)-(2)-(3)-(4)-(5), whereby layer (1) is bound through the open mesh to the charcoal fabric and, in the area surrounding the charcoal fabric (4), to layer (5).

11. A wound dressing according to claim 2 characterized by water vapor transmission of 200 to 2000 g/m$^2$/24 h at 100% relative humidity and 37° C.

12. A wound dressing according to claim 3 characterized by water vapor transmission of 200 to 2000 g/m$^2$/24 h at 100% relative humidity and 37° C.

13. A wound dressing according to claim 4 characterized by water vapor transmission of 200 to 2000 g/m$^2$/24 h at 100% relative humidity and 37° C.

14. A wound dressing according to claim 2 wherein the electrically-conductive mesh comprises a silver-impregnated material.

15. A wound dressing according to claim 3 wherein the electrically-conductive mesh comprises a silver-impregnated material.

16. A wound dressing according to claim 4 wherein the electrically-conductive mesh comprises a silver-impregnated material.

17. A wound dressing according to claim 5 wherein the electrically-conductive mesh comprises a silver-impregnated material.

18. A wound dressing according to claim 2 provided with means for applying a voltage.

19. A wound dressing according to claim 3 provided with means for applying a voltage.

20. A wound dressing according to claim 4 provided with means for applying a voltage.

21. A wound dressing according to claim 5 provided with means for applying a voltage.

22. A wound dressing according to claim 6 provided with means for applying a voltage.

23. A wound dressing according to claim 2 wherein the order of the five layers is (1)-(2)-(3)-(4)-(5).

24. A wound dressing according to claim 3 wherein the order of the five layers is (1)-(2)-(3)-(4)-(5).

25. A wound dressing according to claim 5 wherein the order of the five layers is (1)-(2)-(3)-(4)-(5).

26. A wound dressing according to claim 6 wherein the order of the five layers is (1)-(2)-(3)-(4)-(5).

27. A wound dressing according to claim 7 wherein the order of the five layers is (1)-(2)-(3)-(4)-(5).

* * * * *